United States Patent
Leidreiter et al.

(10) Patent No.: US 7,625,853 B2
(45) Date of Patent: Dec. 1, 2009

(54) AQUEOUS SURFACE-ACTIVE FORMULATION INCLUDING POLYPROPYLENE GLYCOL(3) MYRISTYL ETHER

(75) Inventors: Holger Leidreiter, Hattingen (DE); Uta Kortemeier, Düsseldorf (DE)

(73) Assignee: Evonik Goldschmidt GmbH, Essen (DE)

( * ) Notice: Subject to any disclaimer, the term of this patent is extended or adjusted under 35 U.S.C. 154(b) by 0 days.

(21) Appl. No.: 12/176,690

(22) Filed: Jul. 21, 2008

(65) Prior Publication Data
US 2009/0023622 A1  Jan. 22, 2009

(30) Foreign Application Priority Data
Jul. 20, 2007  (DE) .................. 10 2007 034438

(51) Int. Cl.
*C11D 1/72* (2006.01)
*C11D 1/12* (2006.01)
*C11D 1/90* (2006.01)
*C11D 3/37* (2006.01)
*A61K 8/40* (2006.01)
*A61K 8/46* (2006.01)

(52) U.S. Cl. .................. 510/155; 510/123; 510/125; 510/137; 510/156; 510/159; 510/421; 510/426; 510/433; 510/437; 424/70.1; 424/70.21; 424/70.22; 424/70.31

(58) Field of Classification Search .................. 510/123, 510/125, 137, 155, 156, 159, 421, 426, 433, 510/437; 424/70.1, 70.21, 70.22, 70.31
See application file for complete search history.

(56) References Cited

U.S. PATENT DOCUMENTS 6,159,479 A * 12/2000 Pinzon ..................... 424/401
7,087,221 B2    8/2006 Royce et al.
2004/0115155 A1* 6/2004 Salvador et al. ......... 424/70.13

FOREIGN PATENT DOCUMENTS

DE    4009533 A1   9/1991
EP    0365160 A2   4/1990
EP    0459769 A2   12/1991

(Continued)

OTHER PUBLICATIONS

European Patent Application Publication No. 0 365 160 A3 dated Apr. 25, 1990, English-language abstract only.

*Primary Examiner*—Brian P Mruk
(74) *Attorney, Agent, or Firm*—Scully, Scott, Murphy & Presser, P.C.

(57) ABSTRACT

The present invention relates to the use of polypropylene glycol(3) myristyl ether as preferably the sole viscosity regulator, care active ingredient and solubilizer in aqueous surface-active formulations, preferably having a water content of at least 75% by weight. The present invention further provides aqueous surface-active formulations comprising at least 0.5% by weight, preferably at least 2% by weight, of polypropylene glycol(3) myristyl ether, at least 5% by weight, preferably at least 10% by weight, of at least one surfactant and at least 75% by weight, preferably at least 85% by weight, of water and liquid body cleansing compositions, in particular shower baths and hair shampoos, comprising such an aqueous surface-active formulation.

8 Claims, 1 Drawing Sheet

FOREIGN PATENT DOCUMENTS

| | | |
|---|---|---|
| EP | 0615748 A1 | 9/1994 |
| EP | 1316307 A1 | 6/2003 |
| EP | 1407761 A1 | 4/2004 |
| WO | WO9913857 | 3/1999 |
| WO | WO 01/56537 * | 8/2001 |
| WO | WO0156537 A1 | 8/2001 |

* cited by examiner

AQUEOUS SURFACE-ACTIVE FORMULATION INCLUDING POLYPROPYLENE GLYCOL(3) MYRISTYL ETHER

FIELD OF THE INVENTION

The present invention relates to aqueous surface-active formulations, in particular liquid body cleansing compositions, such as, for example, shower baths and hair shampoos. The present invention also relates to the use of polypropylene glycol(3) myristyl ether as preferably the sole viscosity regulator, care active ingredient and solubilizer in aqueous surface-active formulations, such as shower baths and hair shampoos.

BACKGROUND OF THE INVENTION

Modern cosmetic cleansing products for skin and hair, such as, for example, shower baths and hair shampoos, consist essentially of
  water as the most important solvent,
  surfactants,
  viscosity regulators for thickening the formulation,
  solubility promoters (solubilizers) for water-insoluble substances,
  perfume oils,
  preservatives and
  active ingredients for the care of skin and hair, such as, for example, refatting agents.

Typical surfactants in body cleansing compositions are of anionic, amphoteric and zwitterionic structure. The anionic surfactants include, in particular, the salts of various cations (sodium, ammonium or others) of lauryl sulfate, lauryl ether sulfate, myristyl ether sulfate etc. The zwitterionic surfactants used are, inter alia, cocamidopropylbetaine or cocoamidopropylsultaine. Amphoteric surfactants are, in particular, amphoacetates, such as sodium cocoamphoacetate or disodium cocoamphodiacetate.

Typical thickeners used according to the prior art are NaCl, low molecular weight nonionic surfactants, such as coconut fatty acid monoethanolamide/diethanolamide and laureth-3, or polymeric, high molecular weight, associative, highly ethoxylated fatty derivatives, such as, for example, polyethylene glycol(9000)-hydrogenated glycerol palmitate.

Within the meaning of the present invention, solubilizer or solubility promoter is the term used to refer to a substance which is able to dissolve water-insoluble compounds in aqueous systems to give as clear a solution as possible. According to generally accepted opinion, in this process, micelles are formed, in whose liquid-crystalline structure the hydrophobic substances are integrated. The formation of a "microemulsion", i.e., a thermodynamically stable mixture of water (aqueous solution), an oil (substance immiscible with water) and a solubilizer/solubility promoter is optimal. Typical solubilizers are ethoxylated fatty derivatives.

Perfume oils are generally added to the formulations to improve the olfactory properties. Acceptance by the consumer plays the most important role here. In addition, it is possibly advantageous to mask the intrinsic odors of raw materials used with perfume oils.

Preservatives are used for microbiological stabilization. In the case of contamination, these ingredients (i.e., preservatives) should prevent microbial growth and optionally also kill germs. Preservatives are described in detail and regulated in official regulations (e.g., EU Cosmetics Ordinance).

Typical care additives are ethoxylated glycerol fatty acid esters, such as, for example, polyethylene glycol(7) glyceryl monococoate, or cationic polymers, such as, for example, polyquaternium-7. During skin cleansing, besides the lipophilic dirt, endogenous lipids are also washed away by the surfactants used. This effect is often perceived as unpleasant; that is the skin feels rough and harsh. The skin is also referred to as "dry", although what is meant here is the absence of fat.

So-called refatting agents are added to body cleansing compositions so that the described defatting process is lessened. As a result, on the one hand, the washed-off fat can be replaced by the refatting agent, but on the other hand, the defatting effect of the formulation per se can also be lessened through the use of the refatting agent.

From a formulation point of view, it is difficult to use emollients (cosmetic oils), such as, for example, isopropyl myristate (TEGOSOFT M®), for this purpose because these oils have to be solubilized in a complex manner. More customary refatting agents are therefore relatively hydrophilic products, such as, for example, polyethylene glycol(7) glyceryl monococoate (TEGOSOFT GC®) which are already stabilized through the excess of the cleansing surfactants. Analysis of a product database which gathers worldwide product innovations in consumer markets ("Global New Products Database": Mintel) revealed that 29% of all skin cleansing formulations in the European market in the period of investigation (9/05-9/06) comprised polyethylene glycol (7) glyceryl monococoate.

It is assumed that the refatting process takes place upon rinsing off the formulation after the actual washing. During the rinsing process with water, the solution present is diluted until the so-called CMC (critical micelle concentration) is reduced. With the release of the micelle components (the lipophilic refatting agents, the surfactants and solubilizers), the refatting agents become insoluble again. These lipophilic substances (both endogenous lipids and also emollients/cosmetic oils) precipitate out and attach to the skin.

Besides the cleansing effect, the requirements of the finished formulation thus include a creamy foam, protection against the drying out of the skin and a good care performance. The basic requirements for the individual constituents include good skin compatibility and processability. It would therefore be advantageous if as many of the requirements for a cosmetic formulation as possible could be satisfied by the fewest possible toxicologically acceptable and universally usable constituents.

DE-A 40095533 describes foam-suppressed nonionic surfactant mixtures comprising 20 to 98% by weight of an alkyl polyglycoside and 80 to 2% by weight of a polyglycol ether. The latter component is added to the surfactant mixture on account of its foam-suppressing effect. The polyglycol ethers preferably used also include alkyl ethers of propoxylated fatty alcohols. However, polypropylene glycol(3) myristyl ether is not explicitly mentioned in the entire printed specification. The liquid washing compositions produced using the prior art disclosed surfactant systems also comprise a large number of additional components, and there is no indication at all that the polyglycol ethers used perform further functions in the particular washing composition formulation besides their foam-suppressing effect. Furthermore, the washing composition systems specified by way of example differ from the formulations according to the invention by virtue of their comparatively low water content, at about 35% by weight.

EP-A 0459769 discloses cleansing compositions, in particular soap bars, which exhibit reduced softening and increased gentleness. The described compositions comprise alkali metal salts of higher fatty acids in an amount greater than 25% by weight, 1-50% by weight of a further surfactant, 1-15% by weight of a free fatty acid, and 1-15% by weight of a component which reduces softening. These components also include the alkyl ethers of alkoxylated fatty alcohols, such as, for example, polypropylene glycol(3) myristyl ether. However, further modes of action are not specified. It is also obvious that the disclosed cleansing compositions differ significantly from the compositions according to the invention on account of their very low water content (about 10% by weight).

EP-A 1407761 describes aqueous alcoholic compositions, for example disinfection solutions, which comprise alcohol and water in a weight ratio of from 60:40 to 100:0, and between 0.5 and 8% by weight of a thickener system comprising at least one emulsifier. A large number of further constituents may be present in the aqueous-alcoholic compositions, including emollients, such as polypropylene glycol (3) myristyl ether. Even though the specification indicates that, although a thickener system may be responsible for the stability and consistency of the described compositions, emollients could also influence the viscosity and stability of the compositions, an effect cannot be deduced from the experimental data. Also, when evaluating the described effects, the sometimes extremely high alcohol content of the investigated systems must not be disregarded.

Finally, U.S. Pat. No. 7,087,221 discloses aqueous shampoo compositions with improved hair-conditioning properties comprising at least 20% by weight of water, between 5 and 50% by weight of a surfactant and at least 0.05% by weight of a polyalkylene oxide alkyl ether, which should have an HLB value (hydrophilic-lipophilic balance) of less than 10. Polypropylene glycol(3) myristyl ether is not given under the compounds specified by way of example. The large number of possible further components and also the complex test formulations illustrate that in the '221 patent there is also no teaching which could be associated with the object underlying the present invention.

Thus, none of the cited specifications discloses the use of emollients, in particular polypropylene glycol(3) myristyl ether, as viscosity regulator, care active ingredient or solubilizer in aqueous surface-active formulations.

SUMMARY OF THE INVENTION

The present invention provides a substance which can be used not only as the sole viscosity regulator, but, moreover, brings with it further properties such as good care performance (refatting), good foaming properties and high solubilizing power, so that it is possible to dispense with further viscosity regulators and optionally also with further refatting agents and solubilizers in the particular formulation.

Surprisingly it has been found by the applicant that polypropylene glycol(3) myristyl ether dissolves not only in aqueous surface-active formulations, i.e., surface-active formulations with a water content of at least 75% by weight, without further auxiliaries, but, moreover, also increases the viscosity of the formulation, improves the foam creaminess and the skin feel during application and has solubilizing properties for water-insoluble substances.

The present invention thus provides the use of polypropylene glycol(3) myristyl ether as preferably the sole viscosity regulator, care active ingredient and solubilizer in aqueous surface-active formulations, preferably with a water content of at least 75% by weight.

The present invention further provides aqueous surface-active formulations comprising, or consisting of, at least 0.5% by weight of polypropylene glycol(3) myristyl ether, at least 5% by weight of at least one surfactant and at least 75% by weight of water. In a preferred embodiment of the invention, the aqueous surface-active formulations comprise at least 2% by weight of polypropylene glycol(3) myristyl ether, at least 10% by weight of at least one surfactant and at least 85% by weight of water.

The present invention further provides liquid body cleansing compositions, in particular shower baths and hair shampoos, comprising one such aqueous surface-active formulation.

DETAILED DESCRIPTION OF THE INVENTION

The present invention, which provides aqueous surface-active formulations including polypropylene glycol(3) myristyl ether as preferably the sole viscosity regulator, care active ingredient and solubilizer, will now be described in greater detail.

As stated above, the present invention relates to the use of polypropylene glycol(3) myristyl ether in aqueous surface-active formulations, such as shower bath formulations and hair shampoos, preferably with a water content of at least 75% by weight. The polypropylene glycol(3) myristyl ether is used in such formulations as preferably the sole viscosity regulator, care active ingredient and solubilizer. In some embodiments of the invention, it is possible to dispense with further viscosity regulators and optionally also with further refatting agents and solubilizers.

In particular, the present invention provides aqueous surface-active formulations comprising, or consisting of at least 0.5% by weight of polypropylene glycol(3) myristyl ether, at least 5% by weight of at least one surfactant and at least 75% by weight of water. In a preferred embodiment of the invention, the aqueous surface-active formulations comprise at least 2% by weight of polypropylene glycol(3) myristyl ether, at least 10% by weight of at least one surfactant and at least 85% by weight of water. The present invention further provides liquid body cleansing compositions, in particular shower baths and hair shampoos, comprising one such aqueous surface-active formulation.

Surfactants preferably used according to the invention are the compounds sodium lauryl ether sulfate and cocamidopropylbetaine, and combinations thereof. In addition, however, it is also possible to use all known surfactants in the formulations/compositions according to the invention. Furthermore, the formulations/compositions according to the invention can comprise the generally customary auxiliaries and additives, e.g., viscosity regulators, solubility promoters (solubilizers), perfume oils, preservatives, and active ingredients for the care of skin and hair, such as, for example, refatting agents. However, according to the invention, preference is given to using polypropylene glycol(3) myristyl ether as the sole viscosity regulator, refatting agent and solubilizer.

The formulations/compositions of the present invention are made using processes well known to those skilled in the art.

Figure 1:
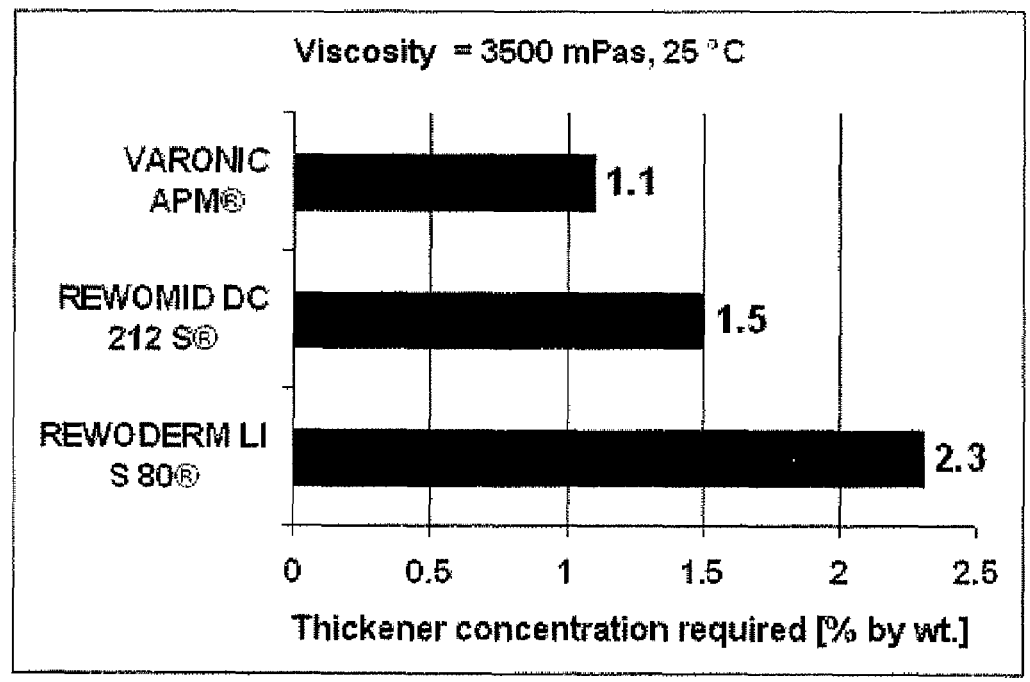
FIG. 1 is a graph illustrating the results of Example 1 relating to the thickening effect of polypropylene glycol(3) myristyl ether vs. two conventional surface-active thickeners.
Figure 2:
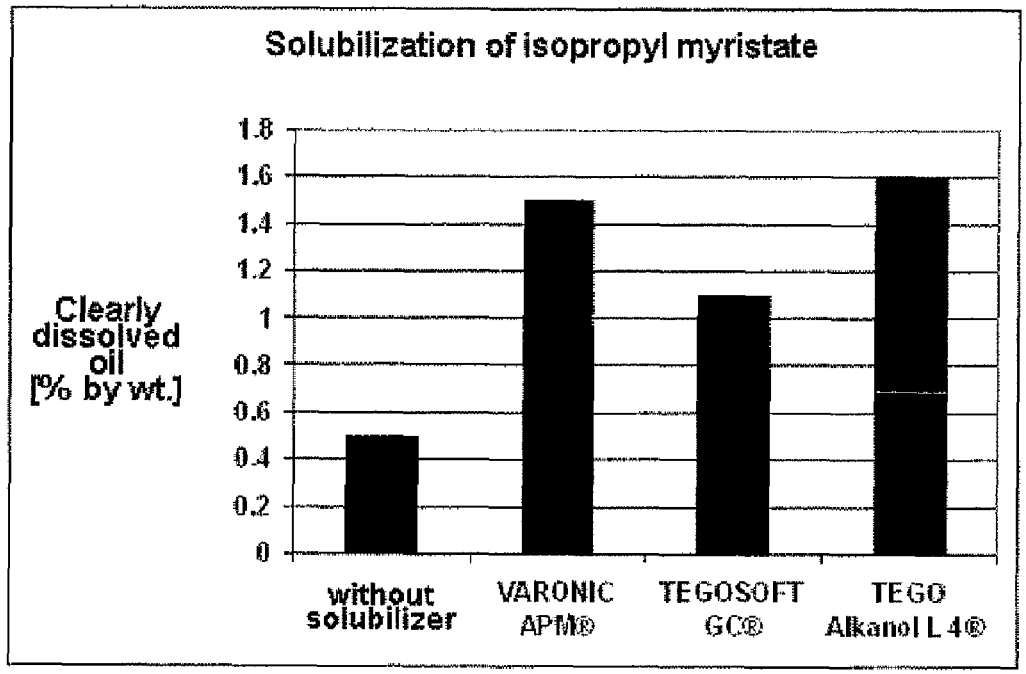
FIG. 2 is a graph illustrating the results of the solubilization experiments according to Example 3.

The present invention is illustrated in more detail by FIG. 1 and FIG. 2 without any intention to restrict the invention to the embodiment depicted therein. FIG. 1 shows in graph form the results of Example 1 relating to the thickening effect of polypropylene glycol(3) myristyl ether. FIG. 2 shows in graph form the results of the solubilization experiments according to Example 3.

The examples below serve to illustrate the present invention, but do not represent any kind of restriction to the scope of protection.

Examples 1a-c

Thickening

The thickening effect of polypropylene glycol(3) myristyl ether (VARONIC APM®) was tested against two customary surface-active thickeners (cocamide DEA (REWOMID DC 212 S®) and polyethylene glycol(9000) hydrogenated glycerol palmitate/polyethylene glycol(7) glyceryl monococoate (REWODERM LI S 80®)). A standardized surfactant system consisting of 9% by weight of sodium lauryl ether sulfate (Texapon NSO®), 3% by weight of cocamidopropylbetaine (TEGO Betain F 50®) and 0.7% by weight of NaCl, was adjusted to a viscosity of 3500 mPas at 25° C. The thickener concentration required in each case for this purpose is shown in Table 1 and also in FIG. 1. It was found that polypropylene glycol(3) myristyl ether (VARONIC APM®) was the most effective since the lowest use concentration was required.

TABLE 1

Thickening effect of polypropylene glycol(3) myristyl ether.

|  | Ex. 1a<br>% by wt. | Ex. 1b*<br>% by wt. | Ex. 1c*<br>% by wt. |
|---|---|---|---|
| Texapon NSO ®<br>(INCI: Sodium Laureth Sulfate) | 9.0 | 9.0 | 9.0 |
| TEGO Betain F 50 ®<br>(INCI: Cocamidopropyl Betaine) | 3.0 | 3.0 | 3.0 |
| VARONIC APM ®<br>(INCI: Polypropylene glycol(3) myristyl ether) | 1.1 | | |
| REWOMID DC 212 S ®<br>(INCI: Cocamide DBA) | | 1.5 | |
| REWODERM LI S 80 ®<br>(INCI: PEG-200 Hydrogenated Glyceryl Palmate/PEG-7 Glyceryl Cocoate) | | | 2.3 |
| NaCl | 0.7 | 0.7 | 0.7 |
| Water, demineralized | | ad 100.0 | |
| Viscosity [mPas], measured at 25° C. using a Brookfield LVF, spindle 3, 5 rpm | | 3500 | |

*comparative example

Examples 2a-g

Skincare Performance and Foam Properties

To evaluate the care performance and the foam properties of polypropylene glycol(3) myristyl ether (VARONIC APM®), sensory handwashing tests compared to polyethylene glycol(7) glyceryl monococoate (TEGOSOFT GC®) were carried out.

Polyethylene glycol(7) glyceryl monococoate serves as a market standard for hydrophilic emollients/refatting agents. A group consisting of 10 trained test subjects washed their hands in a defined way and evaluated foam properties, skin feel and rinse-off behaviour using a grading scale from 1 (poor) to 5 (very good). The products used were tested in each case in two standardized surfactant formulations. Test series 1 was carried out with surfactant system A (sodium lauryl ether sulfate/cocamidopropylbetaine), test series 2 was carried out with surfactant system B (sodium lauryl ether sulfate). Since cocamidopropylbetaine (TEGO Betain F 50®) already has skin-conditioning properties, in test series 2 only the anionic surfactant sodium lauryl ether sulfate (Texapon NSO®) was combined with the emollients. The sensory test results are summarized in Tables 3 and 4.

TABLE 2

Formulations for handwashing test

|  | Test series 1<br>(surfactant system A) | | | | Test series 2<br>(surfactant system B) | | |
|---|---|---|---|---|---|---|---|
|  | Ex. 2a<br>% by wt. | Ex. 2b<br>% by wt. | Ex. 2c*<br>% by wt. | Ex. 2d<br>% by wt. | Ex. 2e<br>% by wt. | Ex. 2f*<br>% by wt. | Ex. 2g<br>% by wt. |
| Texapon NSO ®<br>(INCI: Sodium Laureth Sulfate) | 9.0 | 9.0 | 9.0 | 9.0 | 12.0 | 12.0 | 12.0 |
| TEGO Betain F 50 ®<br>(INCI: Cocamidopropyl Betaine) | 3.0 | 3.0 | 3.0 | 3.0 | | | |
| VARONIC APM ®<br>(INCI: polypropylene glycol(3) myristyl ether | 1.0 | 2.0 | | | 1.0 | | |
| TEGOSOFT GC ®<br>(INCI: PEG-7 Glyceryl Cocoate) | | | 2.0 | | | 1.0 | |
| Water | | | | ad 100.0 | | | |

*comparative example

TABLE 3

Sensory properties - handwashing test with surfactant system A

|  | Ex. 2c* | Ex. 2a | Ex. 2b | Ex. 2d (control) |
|---|---|---|---|---|
| Foaming behaviour | 3.2 | 3.1 | 3.2 | 3.4 |
| Foam volume | 2.9 | 3.0 | 3.2 | 3.3 |
| Foam creaminess | 2.6 | 3.0 | 2.5 | 2.9 |
| Skin feel during washing | 3.3 | 4.0 | 3.8 | 3.6 |
| Ability to be rinsed off | 4.1 | 4.4 | 4.3 | 4.5 |
| Skin smoothness | 2.4 | 2.5 | 2.5 | 2.3 |
| Skin softness | 2.7 | 2.7 | 2.7 | 2.6 |
| Skin smoothness after 3 min | 3.5 | 3.5 | 3.4 | 3.5 |
| Skin softness after 3 min | 3.5 | 3.5 | 3.6 | 3.3 |

*comparative example

Table 3 shows the results of the first test series. Surprisingly, the addition of an emollient reduced the foam quantity but increased the foam quality and improved the skin feel. These desired properties were also found for polypropylene glycol(3) myristyl ether (VARONIC APM®), sometimes significantly more marked than for the market standard polyethylene glycol(7) glyceryl monococoate (TEGOSOFT GC®).

TABLE 4

Sensory properties - handwashing test with surfactant system B

|  | Ex. 2f* | Ex. 2e | Ex. 2g (control) |
|---|---|---|---|
| Foaming behaviour | 3.6 | 3.6 | 3.6 |
| Foam volume | 3.5 | 3.3 | 3.5 |
| Foam creaminess | 2.9 | 2.8 | 2.6 |
| Skin feel during washing | 3.5 | 3.6 | 3.5 |
| Ability to be rinsed off | 4.1 | 4.1 | 4 |
| Skin smoothness | 2.3 | 2.6 | 2.2 |
| Skin softness | 2.6 | 2.9 | 2.6 |

TABLE 4-continued

Sensory properties - handwashing test with surfactant system B

|  | Ex. 2f* | Ex. 2e | Ex. 2g (control) |
|---|---|---|---|
| Skin smoothness after 3 min | 3.5 | 3.4 | 3.2 |
| Skin softness after 3 min | 3.4 | 3.3 | 3 |

*comparative example

Table 4 shows the results of the second test series. The use of only the anionic surfactant led to a lower differentiability in the case of the foam properties, but in the case of skin feel directly after use, polypropylene glycol (3) myristyl ether (VARONIC APM®) exhibited the best results.

In summary, it can be established that polypropylene glycol(3) myristyl ether (VARONIC APM®) had a clearly positive influence both on the foam quality and also on the skin feel during and, especially after use, and sometimes even surpassed the market standard polyethylene glycol(7) glyceryl monococoate (TEGOSOFT GC®).

Examples 3a-k

Solubilizing Properties

The solubilizing properties of polypropylene glycol(3) myristyl ether (VARONIC APM®) were tested by dissolving a water-insoluble oil (isopropyl myristate (TEGOSOFT M®)) in a surfactant solution, consisting of 11.25% by weight of sodium lauryl ether sulfate (Texapon NSO®) and 3.75% by weight of cocamidopropylbetaine (TEGO Betain F 50®) to give a clear solution. For comparison, the oil was dissolved in the pure surfactant solution without the addition of solubilizer. The standards used were the typical solubilizers polyethylene glycol(7) glyceryl monococoate (TECOSOFT GC®) and laureth-4 (TEGO Alkanol L 4®).

Table 5 and FIG. 2 indicate the amount of oil which could be dissolved in the particular system to give a solution which was still clear. Above this amount, clouding resulted.

Polypropylene glycol(3) myristyl ether (VARONIC APM®) had a clear solubilizing effect which surpassed the market standard polyethylene glycol(7) glyceryl monococoate (TEGOSOFT GC®) and was comparable with the likewise customary solubilizer laureth-4 TEGO Alkanol L 4®).

TABLE 5

Formulations and results - solubilization experiments

[% by wt.]

| Example | 3a** | 3b** | 3c | 3d | 3e | 3f* | 3g* | 3h* | 3i* | 3j* | 3k* |
|---|---|---|---|---|---|---|---|---|---|---|---|
| Texapon NSO ® (INCI: Sodium Laureth Sulfate) | 11.25 | 11.25 | 11.25 | 11.25 | 11.25 | 11.25 | 11.25 | 11.25 | 11.25 | 11.25 | 11.25 |
| TEGO Betain F 50 ® (INCI: Cocamidopropyl Betaine) | 3.75 | 3.75 | 3.75 | 3.75 | 3.75 | 3.75 | 3.75 | 3.75 | 3.75 | 3.75 | 3.75 |
| TEGOSOFT M ® (Isopropyl Myristate) | 0.5 | 0.6 | 1.0 | 1.5 | 1.6 | 1.0 | 1.1 | 1.2 | 1.5 | 1.6 | 1.7 |
| VARONIC APM ® |  |  | 0.5 | 0.5 | 0.5 |  |  |  |  |  |  |

TABLE 5-continued

Formulations and results - solubilization experiments

[% by wt.]

| Example | 3a** | 3b** | 3c | 3d | 3e | 3f* | 3g* | 3h* | 3i* | 3j* | 3k* |
|---|---|---|---|---|---|---|---|---|---|---|---|
| (INCI: polypropylene glycol(3) myristyl ether) | | | | | | | | | | | |
| TEGOSOFT GC ® (INCI: PEG-7 Glyceryl Cocoate) | | | | | | 0.5 | 0.5 | 0.5 | | | |
| TEGO Alkanol L 4 ® (INCI: Laureth-4) | | | | | | | | | 0.5 | 0.5 | 0.5 |
| Water | | | | | ad 100.0 | | | | | | |
| Appearance | clear | cloudy | clear | clear | cloudy | clear | clear | cloudy | clear | clear | cloudy |

*comparative example
**control

In summary, it can be stated that the given examples clearly demonstrate the thickening, the care and the solubilizing effect of polypropylene glycol(3) myristyl ether, the effectiveness of the comparison substances (market standards) sometimes being surpassed significantly.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An aqueous surface-active formulation comprising:
   a) at least 5% by weight of at least one surfactant selected from sodium lauryl ether sulfate, cocamidopropylbetaine and combinations thereof;
   b) at least 0.5% by weight of polypropylene glycol(3) myristyl ether; and
   c) at least 75% by weight of water.

2. The aqueous surface-active formulation according to claim 1, wherein said at least one surfactant is present in an amount of at least 10% by weight, said polypropylene glycol (3) myristyl ether is present in an amount of at least 2% by weight, and said water is present in an amount of at least 85% by weight.

3. An aqueous surface-active formulation consisting of:
   a) at least 5% by weight of at least one surfactant;
   b) at least 0.5% by weight of polypropylene glycol(3) myristyl ether; and
   c) at least 75% by weight of water.

4. The aqueous surface-active formulation according to claim 3, wherein said at least one surfactant is present in art amount of at least 10% by weight, said polypropylene glycol (3) myristyl ether is present in an amount of at least 2% by weight, and said water is present in an amount of at least 85% by weight.

5. The aqueous surface-active formulation according to claim 3, wherein the at least one surfactant is selected from sodium lauryl ether sulfate, cocamidopropylbetaine and combinations thereof.

6. A liquid body cleansing composition comprising an aqueous surface-active formulation according to claim 1.

7. The liquid body cleansing composition according to claim 6, wherein the body cleansing composition is a shower bath.

8. The liquid body cleansing composition according to claim 6, characterized in that the body cleansing composition is a hair shampoo.

* * * * *